US00PP21072P3

(12) United States Plant Patent
Álamo et al.

(10) Patent No.: US PP21,072 P3
(45) Date of Patent: Jun. 22, 2010

(54) BLUEBERRY PLANT NAMED 'LUCERO'

(50) Latin Name: ***Vaccinium corymbosum* L.**
Varietal Denomination: Lucero

(75) Inventors: Antonio Abad Álamo, Almonte (ES); José Ulf Hayler López, Almonte (ES); Paul M. Lyrene, Micanopy, FL (US)

(73) Assignee: Royal Berries S.L., Huelva (ES)

( * ) Notice: Subject to any disclaimer, the term of this patent is extended or adjusted under 35 U.S.C. 154(b) by 0 days.

(21) Appl. No.: 12/289,493

(22) Filed: Oct. 29, 2008

(65) Prior Publication Data

US 2009/0210984 P1 Aug. 20, 2009

(30) Foreign Application Priority Data

Feb. 14, 2008 (QZ) ..... PBR20080340

(51) Int. Cl.
*A01H 5/00* (2006.01)

(52) U.S. Cl. ..... Plt./157

(58) Field of Classification Search ..... Plt./157
See application file for complete search history.

*Primary Examiner*—June Hwu
(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers and forms fruit that ripens at mid-season. The attractive light blue substantially round berries are formed in compact clusters and exhibit a refreshing blueberry flavor. The berries are well amenable to mechanical harvest. The plant is self-fertile, and the growth habit is generally upright. Attractive evergreen foliage is displayed. A low chilling requirement is also exhibited.

4 Drawing Sheets

Botanical/commercial classification: *Vaccinium corymbosum* L./Blueberry Plant.

Varietal denomination: cv. Lucero.

SUMMARY OF THE INVENTION

The new Blueberry cultivar of the present invention was the product of controlled artificial pollination carried out in a greenhouse at Greenwood, Fla., U.S.A., wherein two parents were crossed during 1996 which previously had been studied in the hope that they would contribute the desired characteristics. The female parent (i.e., the seed parent) was the unreleased 'FL 91-160' cultivar (non-patented in the United States). The male parent (i.e., pollen parent) was the 'Windsor' cultivar (U.S. Plant Pat, No. 12,783). The parentage of the new cultivar can be summarized as follows:

'FL 91-160'×'Windsor'.

The seeds resulting from the pollination were shipped to Almonte, Huelva, Spain, where they sown during approximately 1997, small plants were obtained which were physically and biologically different from each other and selective research of the progeny was carried out. Selective study resulted in the identification of a single plant of the new cultivar. The new cultivar initially was designated S01-28-01.

It was found that the new Blueberry plant of the present invention displays the following combination of characteristics:

(a) flowers at mid-season and forms fruit that ripens at mid-season, (b) displays a generally upright growth habit with attractive evergreen foliage, (c) is self-fertile, (d) displays a low chilling requirement, and (e) forms in abundance attractive light blue substantially round berries having an extended post-harvest shelf life in compact clusters that exhibit a refreshing blueberry flavor and are well suited for mechanical harvest.

The new cultivar well meets the needs of the horticultural industry and can be grown to advantage for the commercial production of blueberries. The plant is well suited for growing under tunnels in well drained soils in warm regions while utilizing evergreen management techniques.

The new cultivar of the present invention can be distinguished from all other Blueberry cultivars known to its originators. The 'FL 91-160' female parent is extinct and accordingly no longer exists for further comparative purposes by the inventors. Available information indicates that 'FL 91-160' displayed an inferior fruit scar when compared to that of the new cultivar of the present invention. The 'Windsor' male parent displays larger leaves and fragrant flowers, unlike the new cultivar of the present invention. When compared to the 'Sharpblue' cultivar (non-patented in the United States), the new cultivar is taller, more upright, and more resistant to Leaf Rust. When compared to the 'Misty' cultivar (non-patented in the United States), the new cultivar forms very compact berry clusters while the fruit of the 'Misty' cultivar commonly is borne in a considerably more expanded manner. When compared to the 'O'Neal' cultivar (non-patented in the United States), the new cultivar commonly displays a chill requirement of less than 300 hours, while the chill requirement of the 'O'Neal' cultivar commonly approximates 500 hours. When compared to the 'Star' cultivar (U.S. Plant Pat. No. 10,675), the new cultivar commonly is more resistant to Botrytis.

The new cultivar was selected during the spring of 2001 and has been asexually reproduced by the rooting of softwood cuttings beginning during the summer of 2001 at Almonte, Huelva, Spain. Such asexual propagation has shown that the characteristics of the new cultivar are firmly fixed and are stably transmitted from one generation to another. Accordingly, the new cultivar asexually reproduces in a true-to-type manner.

The new cultivar has been named 'Lucero'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants which had been asexually reproduced by the rooting of softwood cuttings were approximately five years of age except where otherwise indicated, and were being grown outdoors at Almonte, Huelva, Spain.

DETAILED DESCRIPTION

Figure 1:
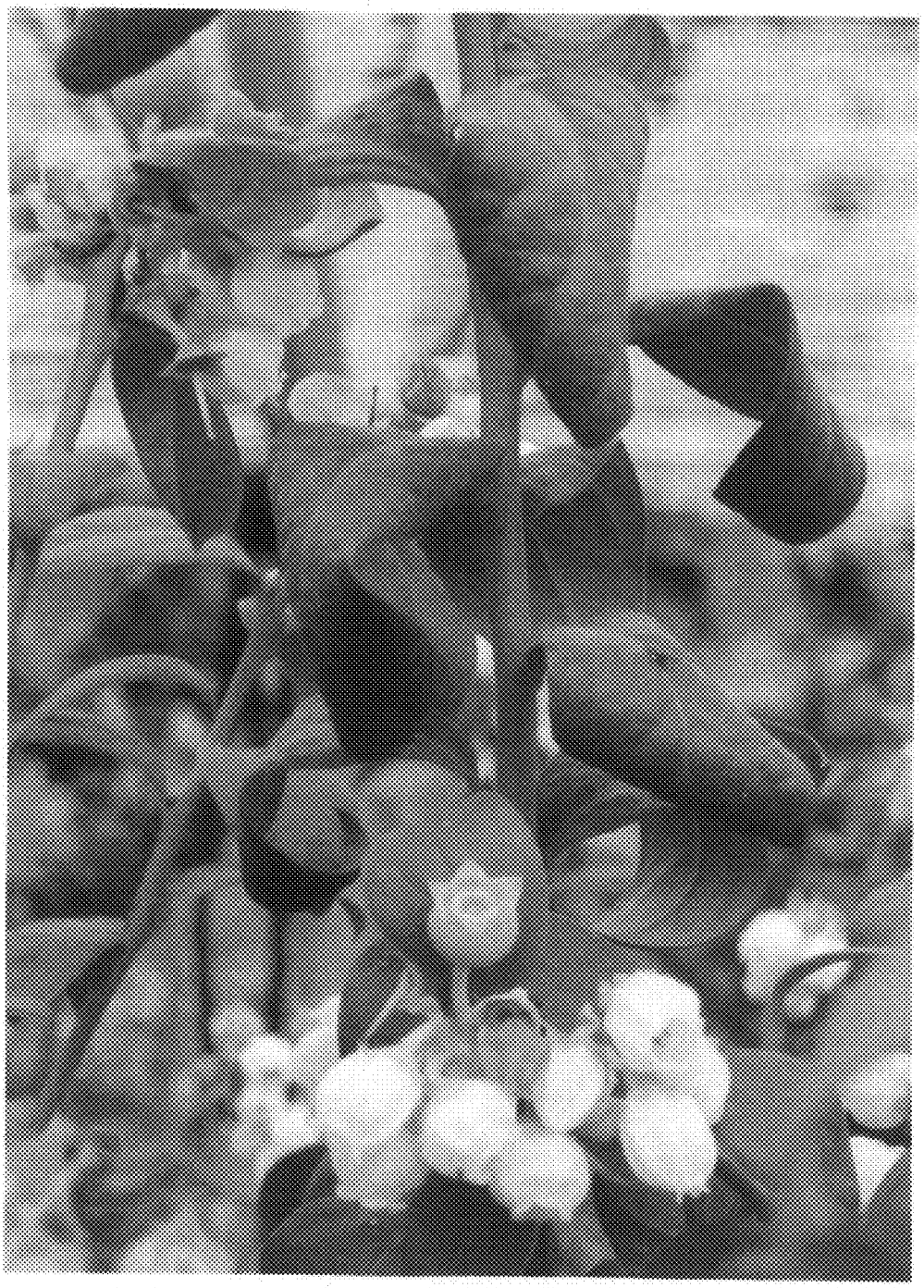
FIG. 1 shows a portion of an upright flowering plant of the new cultivar.
Figure 2:
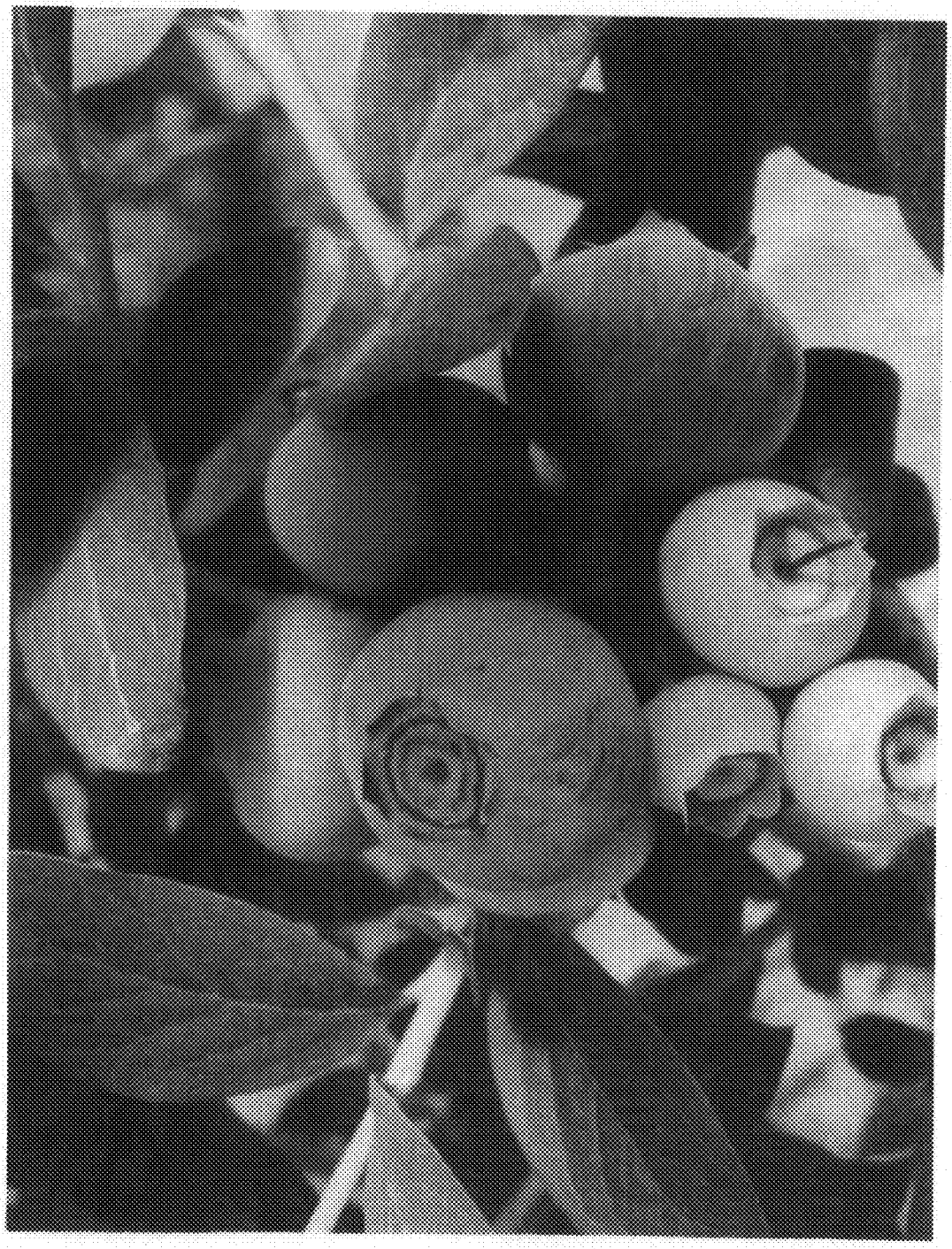
FIG. 2 shows a compact cluster of berries of the new cultivar in various stages of development as well as the foliage of the new cultivar.
Figure 3:
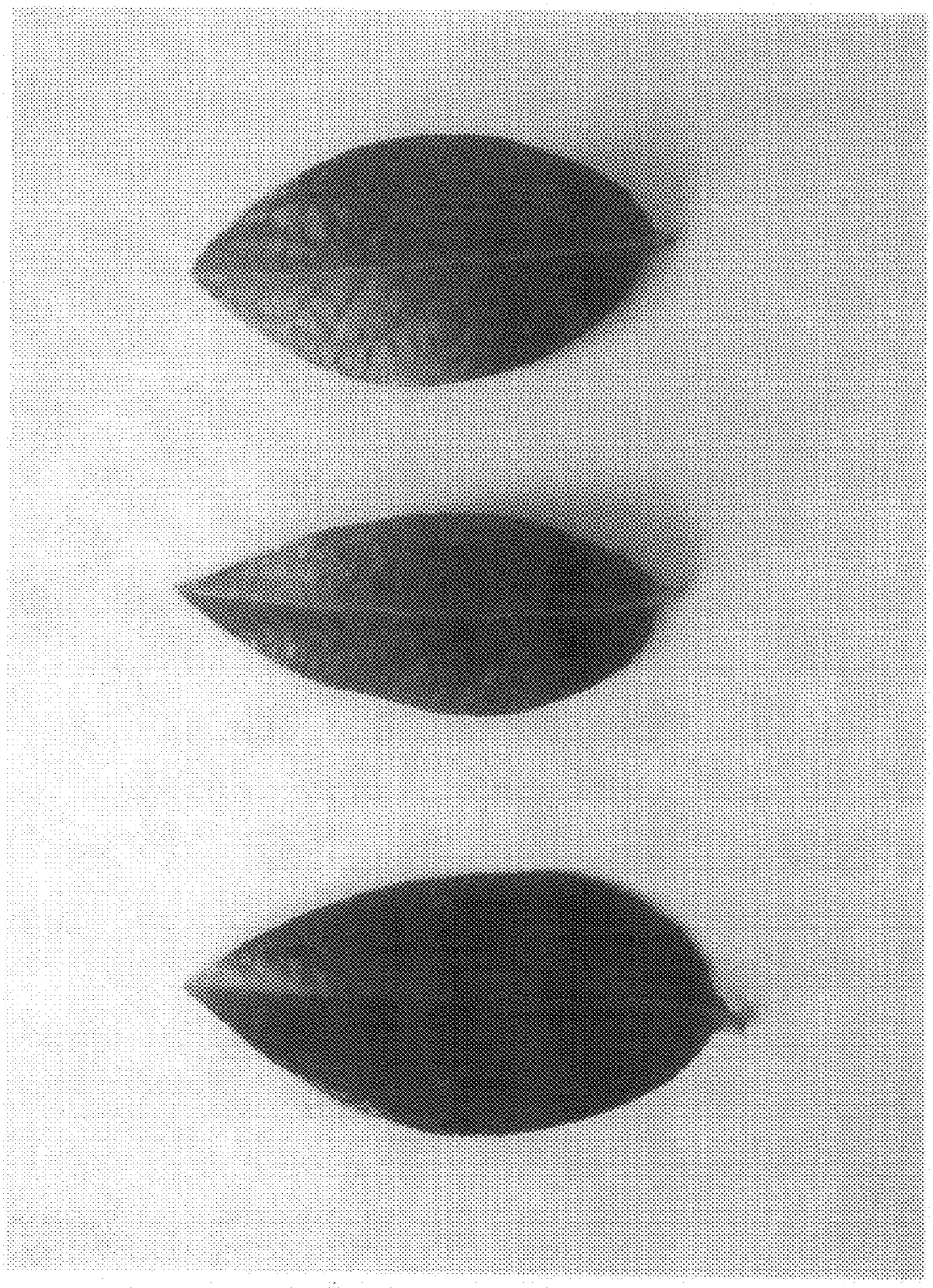
FIG. 3 shows a close view of the upper (adaxial)) surfaces of typical leaves of the new cultivar.
Figure 4:
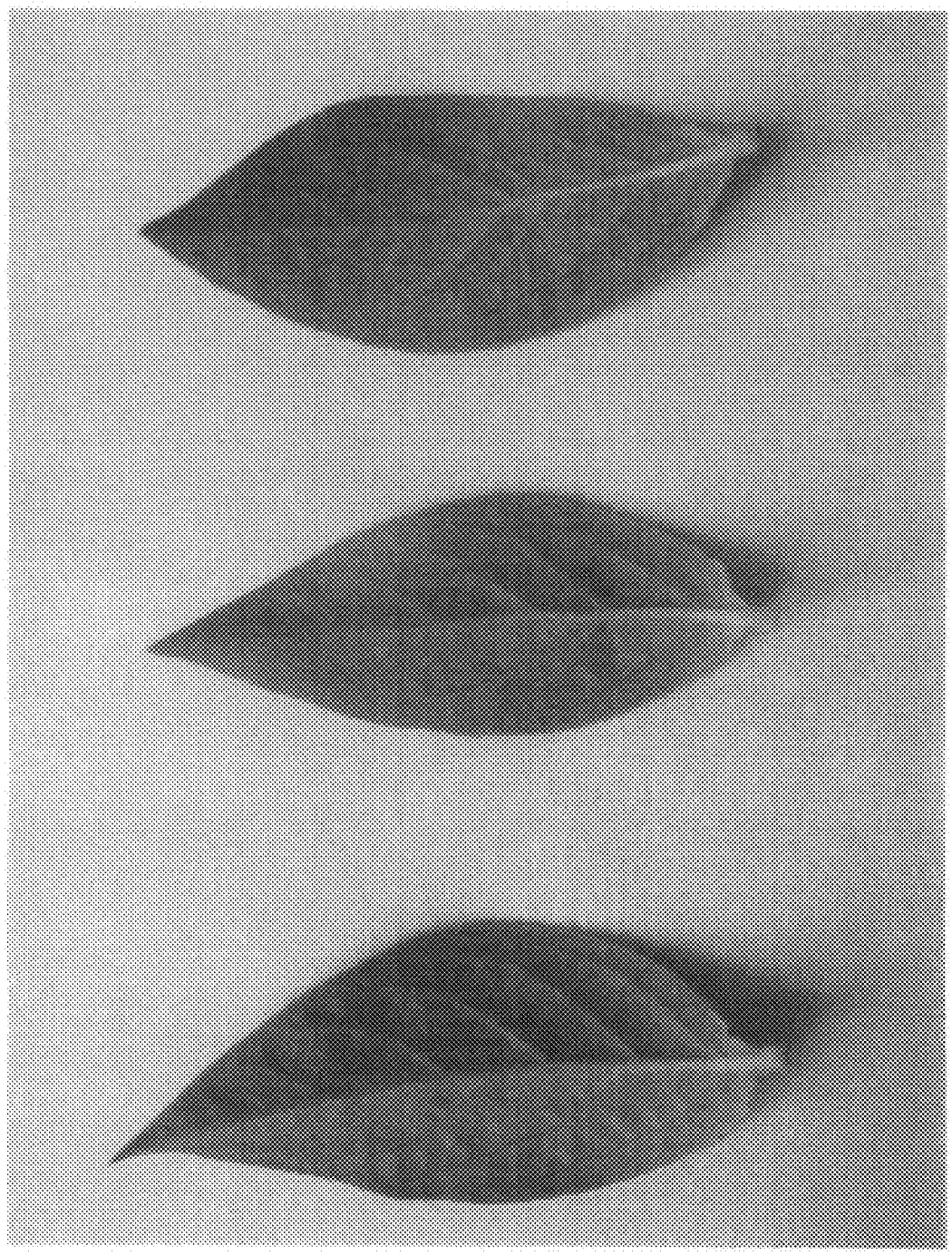
FIG. 4 shows a close view of the under (abaxial) surfaces of typical leaves of the new cultivar.

The chart used in the identification of the colors described herein is the R.H.S. Colour Chart of The Royal Horticultural Society, London, England. Ordinary color terms are to be accorded their customary dictionary significance. The description is based on the observation of approximately five-year-old plants of the new cultivar which had been asexually reproduced by the rooting of softwood cuttings while growing outdoors at Almonte, Huelva, Spain.

Plant:

*Growth habit.*—Generally upright.

*Height.*—Approximately 1.75 m at 5 years of age.

*Width.*—Approximately 2.7 m at 5 years of age.

*Mature canes.*—Commonly approximately 46.6 cm in length on average, approximately 3.2 cm in diameter at the base on average, approximately 2.2 cm in diameter towards the tip on average, and near Grey-Brown Group 199D in coloration.

*Foliage retention.*—Evergreen.

*Chill requirement.*—Less than 300 hours.

Foliage:

*Shape.*—Generally elliptic (as illustrated).

*Length.*—Commonly approximately 59 mm on average.

*Width.*—Commonly approximately 27 mm on average.

*Apex.*—Acute.

*Base.*—Acute.

*Margin.*—Entire.

*Texture.*—Glabrous and non-glandular on both surfaces.

*Color.*—Green Group 137B on the upper (adaxial) surface, and near Green Group 138C on the under (abaxial) surface.

*Petiole.*—Commonly approximately 2.8 mm in length on average, commonly approximately 1.9 mm in diameter on average, near Yellow-Green Group 144D on the upper surface, and near Yellow-Green Group 144C on the under surface.

Flowers:

*Time.*—Mid-season, at Almonte, Huelva, Spain, with first flower commonly at approximately January 20$^{th}$, and 50 percent bloom at approximately February 25$^{th}$.

*Number.*—Commonly approximately 6 flowers per inflorescence on average.

*Petals.*—5 in number and fused into a corolla tube.

*Corolla shape.*—Urceolate.

*Corolla size.*—The corolla tube commonly is approximately 9.9 mm in length on average, and approximately 9.3 mm in width on average at the widest point.

*Corolla color.*—Commonly near Green-White Group 157D.

*Sepals.*—5 in number, and approximately 30 percent of the flowers bear more than 5 sepals, e.g., 6 or 7 sepals.

*Calyx.*—Commonly approximately 2.9 mm in length on average, Green Group 143D on the inner surface, and Green Group 142D on the outer surface.

*Filaments.*—Pubescent, non-adnate, commonly pale green in coloration with some near white filaments similar in coloration to that of the corolla, and approximately 4.8 mm in length on average.

*Anthers.*—Bronze-colored, and the size ratio of the pollen sac:pollen tube commonly is approximately 1:1.

*Pistil.*—One per flower and light green in coloration.

*Style.*—Cone-shaped in configuration, light green in coloration with some slight darkening at the base, approximately 9.7 mm in length on average, and approximately 1 to 2 mm in thickness at the base on average.

*Peduncle.*—Commonly approximately 7.6 mm in length, approximately 1.2 mm in diameter, and Yellow-Green Group 144D in coloration, commonly with some Greyed-Red Group 179A, 179B, 180A, and 180B.

*Fertility.*—Self-fertile.

*Fragrance.*—None.

Fruit:

*Time.*—Commonly from approximately April 20th to June 15$^{th}$ at Almonte, Huelva, Spain (i.e., approximately 8 weeks).

*Shape.*—Substantially round and somewhat pumpkin-shaped (as illustrated).

*Height.*—Commonly approximately 17 mm on average.

*Width.*—Commonly approximately 20 mm on average.

*Weight.*—Approximately 3.26 g/berry on average when plants were 5 years of age.

*Fruit scar.*—Approximately 1.4 mm in size, relatively deep, and dry.

*Seed number.*—Commonly approximately 28 per berry on average.

*Seed size.*—Commonly approximately 1.2 mm in length, and approximately 0.8 mm in width on average.

*Immature color.*—Commonly near Green Group 130D with bloom, and Yellow-Green Group 145A without bloom.

*Mature color.*—Light blue, Violet-Blue Group 97A with bloom, and Black Group 202A without bloom.

*Productivity.*—Abundant, approximately 3.21 Kg/plant on average when plants were 5 years of age.

*Flavor.*—Displays a refreshing blueberry flavor.

Development:

*Ability to store.*—The fruit stores well under refrigeration, when stored at 8° C. approximately 100 percent of harvest commonly is good 7 days after harvest, and when stored at 20° C. approximately 96 percent of harvest commonly is good 7 days after harvest.

*Disease tolerance.*—No special sensitivity to common Blueberry diseases, such as Leaf Rust (*Pucciniastrum vaccini*) and *Botrytis* (*Botrytis cinerea*), has been encountered during observations to date at Almonte, Huelva, Spain, and has shown to be more resistant to Leaf Rust than the 'Sharpblue' cultivar, and more resistant to Botrytis than the 'Star' cultivar.

*Insects.*—Is susceptible to aphids and thrips.

*Cultural conditions.*—Does well when grown in a warm low-chilling area under tunnels in well drained soils while using evergreen growing conditions.

*Heat resistance.*—Heat tolerant, has withstood temperatures as high as 45° C. at Almonte, Huelva, Spain.

*Cold resistance.*—Has withstood temperatures as low as −10° C. at Almonte, Huelva. Spain.

Plants of the 'Lucero' cultivar have not been observed under all possible environmental conditions to date, Accordingly, it is possible that the phenotypic expression may vary somewhat with changes in light intensity and duration, cultural practices, and other environmental conditions without variance in the genotype.

We claim:

1. A new and distinct Blueberry plant that possess the following combination of characteristics:

(a) flowers at mid-season and forms fruit that ripens at mid-season, (b) displays a generally upright growth habit with attractive evergreen foliage, (c) is self-fertile, (d) displays a low chilling requirement, and (e) forms in abundance attractive light blue substantially round berries having an extended post-harvest shelf life in compact clusters that are well suited for mechanical harvest and exhibit a refreshing blueberry flavor;

substantially as herein shown and described.

* * * * *